United States Patent [19]  
Chan et al.

[11] 4,097,495  
[45] Jun. 27, 1978

[54] TETRAMETHYL-BENZYLOXY CHROMANS

[75] Inventors: Ka-Kong Chan, Stanhope; Gabriel Saucy, Essex Fells, both of N.J.

[73] Assignee: Hoffmann-La Roche Inc., Nutley, N.J.

[21] Appl. No.: 770,540

[22] Filed: Feb. 22, 1977

Related U.S. Application Data

[60] Division of Ser. No. 638,382, Dec. 8, 1975, Pat. No. 4,029,678, which is a continuation-in-part of Ser. No. 544,153, Jan. 27, 1975, Pat. No. 4,000,169.

[51] Int. Cl.$^2$ .......................................... C07D 311/72  
[52] U.S. Cl. .................................................. 260/345.5  
[58] Field of Search ........................... 260/365.5, 345.5

[56] References Cited  
U.S. PATENT DOCUMENTS  
4,003,319  1/1977  Scott et al. ...................... 260/345.5

Primary Examiner—Nicky Chan  
Attorney, Agent, or Firm—Samuel L. Welt; Bernard S. Leon; William H. Epstein

[57] ABSTRACT

A total asymmetric synthesis for producing optically active vitamin E, from 2,5,7,8-tetramethylchroman-2-acetaldehyde including intermediates in this synthesis.

1 Claim, No Drawings

TETRAMETHYL-BENZYLOXY CHROMANS

CROSS REFERENCE TO RELATED APPLICATIONS

This application is a division application of U.S. Pat. application Ser. No. 638,382, Chan et al., filed Dec. 8, 1975, now U.S. Pat. No. 4,029,678, which in turn is a continuation-in-part of U.S. Pat. application Ser. No. 544,153, Chan et al., filed Jan. 27, 1975, now U.S. Pat. No. 4,000,169.

This application is related to U.S. Pat. application Ser. No. 417,465 filed Nov. 19, 1973, now U.S. Pat. No. 3,947,473, Scott, Parrish and Saucy, which is incorporated herein by reference. This application is also related to U.S. Pat. application Ser. No. 544,163 filed Jan. 27, 1975, Cohen and Saucy, now abandoned and U.S. Pat. application Ser. No. 587,570 filed Jun. 17, 1975, Chan and Saucy, now U.S. Pat. No. 4,016,178.

BACKGROUND OF THE INVENTION

In the past, optically active α-tocopheral and derivatives thereof which are the 2R, 4′R, 8′R isomers of compounds of the formula:

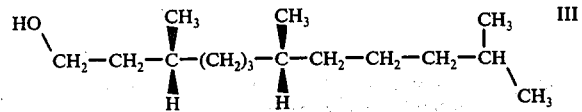

have been prepared through isolation from natural sources such as vegetable oil. This procedure suffers from many drawbacks due to the fact that the tocopherol content of these oils is very small. Therefore, a great amount of oil must be processed in order to isolate a small amount of natural tocopherol. Additionally, the process whereby various tocopherols are isolated from vegetable oil is extremely cumbersome.

In U.S. Pat. application Ser. No. 417,465, filed Nov. 19, 1973, Scott et al., natural α-tocopherol has been synthesized by reacting via a Wittig reaction a compound of the formula:

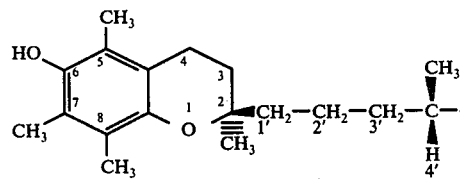

wherein R taken together with its attached oxygen atom forms an ether or ester protecting group removable by hydrogenolysis.
(Please note the compound of formula XXVII-A in U.S. application Ser. No. 417,465, filed Nov. 19, 1973) with a dodecanol of the formula:

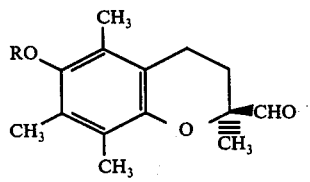

(Please note compound XLVIII-B in U.S. application Ser. No. 417,465). A disadvantage of this process is that the dodecanol of formula III has been difficult to synthesize asymmetrically. In the past, this dodecanol has been produced through degradation of naturally occurring materials such as phytol.

SUMMARY OF THE INVENTION

In accordance with this invention, there is provided another procedure for asymmetrically synthesizing the optically active compound of formula I from the compound of formula II without the need for separating and discarding any unwanted optical isomer.

The new asymmetric synthesis is achieved in accordance with this invention by the discovery that when a compound of the formula:

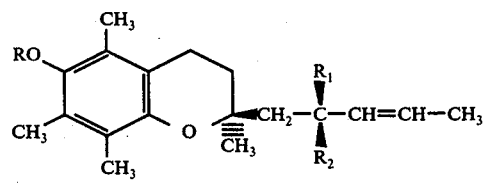

wherein R is as above; one of $R_1$ and $R_2$ is hydroxy and the other is hydrogen; with the proviso that when $R_1$ is hydrogen, the 2-3 double bond has a trans configuration and when $R_1$ is hydroxy, the 2-3 double bond has a cis configuration; is subjected to Claisen rearrangement, an optically active compound of the formula:

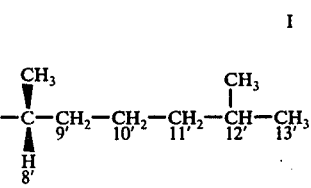

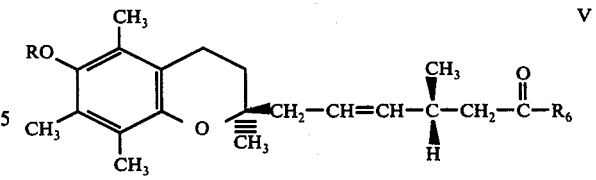

wherein R is as above; $R_6$ is lower alkoxy,

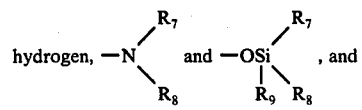

$R_7$, $R_8$ and $R_9$ are lower alkyl;
is formed which can be directly converted into the optically active compound of formula I.

DETAILED DESCRIPTION OF THE INVENTION

The numbering of the chain in formula I, above, is shown for the purpose of convenience.

As used throughout the application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

When the term "cis" is utilized in this application, it designates that the two largest substituents attached across the double bond are on the same side of th double bond. The term "trans" as utilized in this application, designates that the largest substituents attached across the double bond are on opposite sides of the double bond.

In the pictorial representation of the compounds given throughout this application, a (▼) tapered line indicates a substituent which is pointed out of the plane of the paper towards the reader.

The term "lower alkoxy" as used throughout the specification denotes lower alkoxy groups containing from 1 to 7 carbon atoms such as methoxy, ethoxy, propoxy, isopropoxy, etc. The term "lower alkanoyl" as used throughout the specification denotes lower alkanoyl groups containing from 2 to 6 carbon atoms such as acetyl or propionyl.

In accordance with this invention, the compound of formula II is converted to the compound of formula V via the following intermediates:

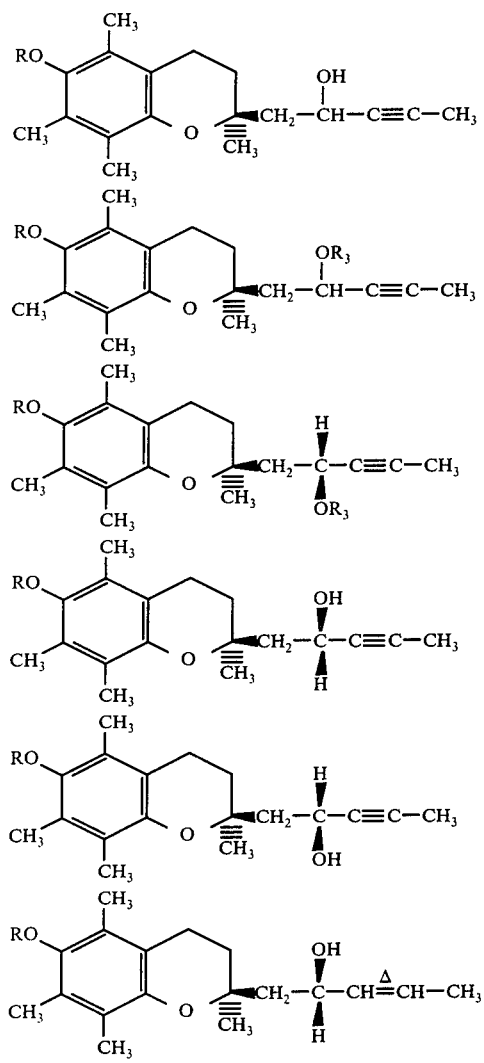

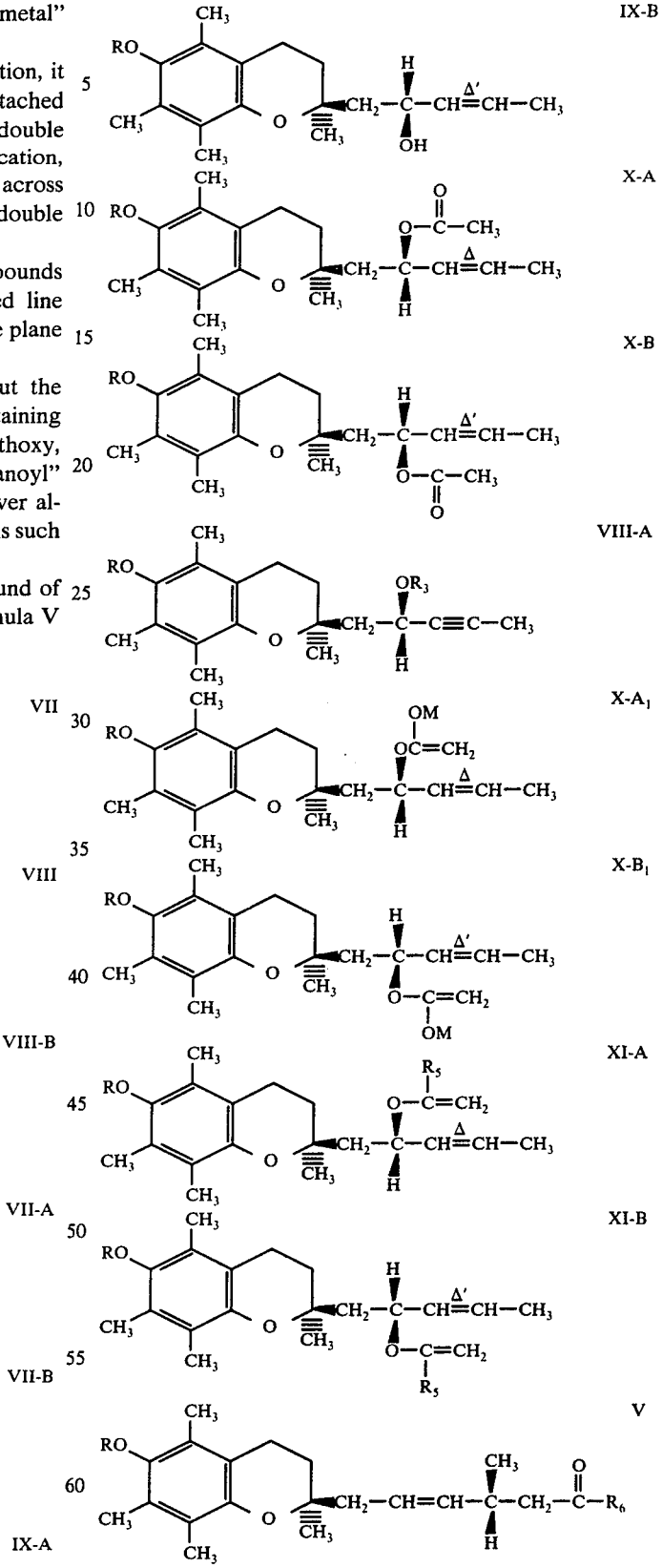

wherein R and $R_6$ are as above; M is an alkali metal; $R_3$ is a radical derived from an aromatic carboxylic acid by removal of the hydroxy moiety of the carboxylic acid group; $R_5$ is hydrogen, lower alkoxy,

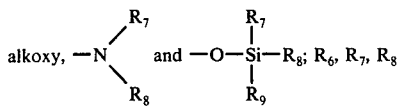

and $R_9$ are as above; $\Delta$ designates that the double bond has a cis configuration and $\Delta'$ designates that the double bond has a trans configuration.

In the first step of this invention, the compound of the formula:

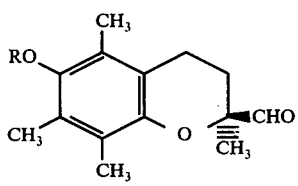

is converted to the compound of formula VII by reacting the compound of formula I with a compound of the formula:

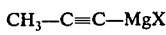

wherein X is a halogen; via a Grignard reaction. Any of the conditions conventional in Grignard reactions can be utilized carrying out this reaction.

The compound of formula VII can be separated into its diastereoisomers i.e., the compounds of formula VII-A and VII-B by fractional crystallization. Any of the conventional methods and techniques of fractional crystallization can be utilized to carry out this separation.

On the other hand, the compound of formula VII can be separated into its diastereoisomers, i.e., the compound of formula VII-A and VII-B, through the reaction of the compound of formula VII with an aromatic carboxylic acid to form a crystallizable ester followed by fractional crystallization. The formation of the esters of formula VIII-A and VIII-B is carried out by conventional means such as by reaction with a reactive derivative of an aromatic carboxylic acid such as 3,5-dinitrobenzoic acid, p-nitrobenzoic acid or benzoic acid. The esters of formula VIII-A and VIII-B are separated by fractional crystallization. Any conventional method of fractional crystallization can be utilized.

The compound of formula VII-A amd VII-B can be obtained from the compounds of formula VIII-A and VIII-B by alkaline hydrolysis. Any conventional method of alkaline hydrolysis can be utilized to effect this conversion.

The compounds of formula VIII-A and VIII-B are converted into the compounds of the formula VII-A and VII-B respectively. This conversion is generally carried out by ester hydrolysis. Any conventional method of ester hydrolysis can be utilized to carry out this conversion. A preferred method is carrying out this reaction in the presence of a base such as an alkali metal hydroxide base in an aqueous medium.

The compound of formula VII-A is converted to the compound of the formula IX-A by hydrogenation in the presence of a selective hydrogenation catalyst. Any conventional catalyst which selectively reduces only the triple bond (acetylene linkage) to a double bond can be utilized in carrying out this conversion. Among the preferred selective hydrogenation catalysts are the palladium catalysts which contain a deactivating material such as lead, lead oxide or sulfur. Among the preferred selective hydrogenation catalysts are included the palladium-lead catalysts of the type disclosed in Helvetica Chemica Acta., 35, pg. 446 (1952) and U.S. Pat. No. 2,681,938 — Lindlar. In carrying out this hydrogenation, temperature is not critical and this reaction can be carried out at room temperature. On the other hand, elevated or reduced temperatures can be utilized. Generally, this reaction is carried out in an inert organic solvent. Any conventional inert organic solvent can be utilized such as n-hexane, ethyl acetate, toluene, petroleum ether or methanol. The selective hydrogenation of a compound of the formula VII-A utilizing a selective hydrogenation catalyst produces a cis configuration across the double bond formed thereby. Therefore, the subjection of a compound of the formula VII-A to catalytic hydrogenation produces a compound of the formula IX-A where the double bond formed by the selective hydrogenation has a cis configuration.

In accordance with this invention, the compound of formula VII-B is converted to the compound of formula IX-B by chemical reduction with either sodium in liquid ammonia or an aluminum hydride reducing agent. The chemical reduction of the compound of formula VII-B reduces the triple bond to a double bond which has a trans configuration. Hence, the compound of formula IX-B is formed by this chemical reduction with the double bond having a trans configuration. Where the reduction is carried out utilizing sodium in liquid ammonia, any of the conditions conventional in this type of reduction can be utilized. Generally, this reaction is carried out at a temperature of from about $-30°$ C. to $-80°$ C. In this reduction, the liquid ammonia can be utilized as the reaction medium. On the other hand, a co-solvent can be present in the reaction medium along with liquid ammonia. As the co-solvents, any conventional inert organic solvent which is in liquid form at the temperature of the reaction can be utilized. Among the preferred inert organic solvents are included ether solvents such as diethyl ether, tetrahydrofuran, etc. On the other hand, the reduction can be carried out by treating the compound of formula VII-B with an aluminum hydride reducing agent. Any conventional aluminum hydride reducing agent can be utilized to carry out this reduction. Among the preferred reducing agents are the alkyl aluminum hydrides reducing agents such as diisobutyl aluminum hydride, diisoamyl aluminum hydride, etc. as well as sodium bis-[2-methoxyethoxy]-aluminum hydride. The reduction with an aluminum hydride reducing agent is carried out in an inert organic solvent medium. Any conventional inert organic solvent medium can be utilized for carrying out this reaction. Among the preferred inert organic solvents are included tetrahydrofuran, pentane, dioxane, diethylether, hexane, toluene, benzene or xylene. Generally, temperatures of from about $-120°$ C. to about $140°$ C. are utilized in carrying out this reduction reaction.

In accordance with this invention, when the compound of formula IX-A or IX-B is subjected to Claisen rearrangement, the compound of formula V is produced. In accordance with this invention, it has been found that both of the compounds of formula IX-A and IX-B undergo Claisen rearrangement to produce the compound of formula V. The compound of formula IX-A is converted to the compound of formula V via an intermediate of the formula XI-A and the compound of formula IX-B is converted to the compound of formula V via an intermediate of the formula XI-B. Any of the conditions conventional in Claisen rearrangement can be utilized in carrying out the conversion of either the compound formed by the compound of the formula IX-A or IX-B to a compound of the formula V. It is known that Claisen rearrangements occur asymmetrically. See Hill et al., *J. Org. Chem.*, Vol. 37, No. 32, 1972, pages 3737–3740, as well as Sucrow et al., *Chem. Ber.*, 104, 3689–3703 (1971), and Sucrow and Richter, *Chem. Ber.*, 104, 3679–3688 (1971). However, in the substrates utilized as starting materials in the Claisen rearrangements disclosed by Hill, asymmetric induction depends upon the presence of the optically active asymmetric carbon atom in the starting material. On the other hand, in accordance with this invention, in order to obtain by asymmetric induction through the Claisen rearrangement the desired isomer which can be converted to optically active natural vitamin E, both the proper optical configuration about the asymmetric carbon atom and the proper geometric configuration about the double bond must be present in the starting material. If the compound of the formula IX-A or IX-B is utilized in the form of a mixture of optical isomers or geometric isomers or both, one will not obtain the proper asymmetric induction through the Claisen rearrangement reaction to intermediate the intermeidate of formula V which can be converted directly to optically active natural vitamin E.

The compounds of formula IX-A and IX-B are converted via the Claisen reaction to the compound of formula V via the intermediates in the formula of XI-A and XI-B. In carrying out this reaction, any of the conditions conventionally utilized in Claisen type rearrangement reaction such as described in the above publications can be utilized. In accordance with the preferred embodiment of this invention, the Claisen rearrangement is carried out by reacting the compounds of formula IX-A or IX-B with any one of the following reactants:

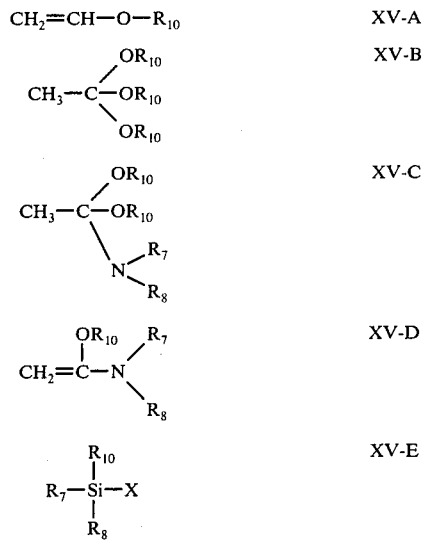

wherein $R_7$ and $R_8$ are as above, and $R_{10}$ is lower alkyl, and X is halogen.

The compound of formula V where $R_6$ is hydrogen can be formed by reacting either the compound of formula IX-A or IX-B with the vinyl ether of formula XV-A via a Claisen rearrangement reaction. Any of the conditions conventional in carrying out a Claisen rearrangement with a vinyl ether can be utilized in carrying out this reaction. Where the compound of formula IX-A is utilized, the compound of formula XI-A where $R_5$ is hydrogen is formed as an intermediate. On the other hand, where the compound of formula IX-B is utilized as the starting material, the compound of the formula XI-B where $R_5$ is hydrogen is formed as an intermediate. In converting the compound of formula IX-A and IX-B to the compound of formula XI-A and XI-B respectively, the compound of formula IX-A or IX-B is first reacted with the vinyl ether of formula XV-A. In reacting either the compound of the formula IX-A or IX-B with the compound of formula XV-A to form the compound of formula XI-A and XI-B where $R_5$ is hydrogen, temperatures of from about 40° C. to 150° C. are generally utilized. This reaction takes place in the presence of an acid catalyst. Any conventional acid catalyst can be utilized. Among the preferred acid catalysts are the inorganic acids such as phosphoric acid and the hydrohalic acids as well as acid salts such as mercuric acetate. On the other hand, conventional organic acid catalysts such as p-toluene sulfonic acid and p-nitrophenol can be utilized. This reaction can be carried out in an inert organic solvent. Any conventional inert organic solvent having a boiling point of greater than 40° C. can be utilized. Among the preferred solvents are the high boiling hydrocarbon solvents such as benzene, toluene, xylene, heptane, as well as ether solvents such as dimethoxyethane, diethylene glycoldimethyl ether and dioxane. The compound of formula XI-A or XI-B where $R_5$ is hydrogen can be converted to the compound of formula V where $R_6$ is hydrogen by heating to a temperature of from 80° C. to 200° C. This reaction is carried out in the absence of any catalyst. However, the same solvent medium utilized for forming the compounds of formulas XI-A or XI-B can be utilized in carrying out this reaction.

On the other hand, the compounds of formula IX-A and IX-B can be converted to the compound of formula V utilizing the orthoacetate of formula XV-B. In carrying out this reaction, any of the conditions conventionally used in Claisen rearrangements with this orthoacetate can be utilized. Where the compound of formula IX-A is utilized, the compound of formula XI-A where $R_5$ is lower alkoxy forms as an intermediate. On the other hand, where the compound of formula IX-B is utilized, the compound of formula XI-B forms as an intermediate. Under the conditions of this reaction, the compound of formula XI-A and the compound of formula XI-B where $R_5$ is lower alkoxy rearranges instantaneously to produce the compound of the formula V where $R_6$ is lower alkoxy. In carrying out this reaction, temperatures of from 140° C. to 250° C. are generally utilized. This reaction is carried out in the presence of excess of the orthoacetate of formula XV-B. This is true since the orthoacetate can be utilized as the solvent medium. On the other hand, the reaction can take place in an inert organic solvent, generally those solvents having a boiling point of greater than 140° C. are preferred. Generally it is preferred to carry out this reaction in the presence of a lower alkanoic acid. If desired, the lower alkanoic acid is present in molar amounts of from about 1% to 10% per mole of the compound of formula IX-A or IX-B utilized as the starting material.

Where it is desired to produce the compound of formula V where $R_6$ is
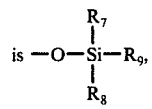

the compounds of formula IX-A and IX-B are first converted to the compounds of formula X-A and X-B respectively via acetylation with an acetic acid or reactive derivatives thereof. Any conventional method of esterifying a hydroxy group with an acetyl group can be utilized to carry out this conversion. Among the preferred methods is to react the compound of formula X-A or X-B with a reactive derivative of an acetic acid such as a halide derivative or an anhydride derivative. The compounds of formula X-A and X-B in their enolate form are then reacted with a compound of the formula XV-E to form the compound of the formula V via a Claisen reaction. The enolates of the compound of formula X-A and X-B which are the compounds of formula X-A₁ and X-B₁ are produced by reacting the compounds of formula X-A and X-B respectively with an alkali metal alkyl amide base. Any conventional alkali metal alkyl amide can be utilized. The alkyl moiety can be a lower alkyl or cycloalkyl moiety which contains from 5 to 7 carbon atoms. Among the preferred bases are lithium isopropyl cyclohexyl amide and lithium diisopropyl amide. Upon reaction of the enolate of formula X-A₁ and X-B₁ with the silyl halide of formula XV-E, compounds of the formula XI-A or XI-B form, where $R_5$ is
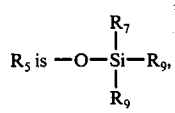

as intermediates. This reaction takes place utilizing the conditions conventional in Claisen type reactions with alkyl silyl halides. Generally, the enolates of formula X-A₁ or X-B₁ are reacted with the silyl halide in an inert organic solvent medium at a temperature of from −10° C. to −110° C. In carrying out this reaction, any conventional inert organic solvent which will not freeze at the reaction temperature can be utilized. Among the preferred solvents are tetrahydrofuran and diethyl ether.

The compounds of formula XI-A and XI-B where $R_5$ is

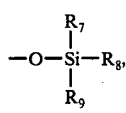

are converted to the corresponding compound of formula V by warming either the compound of formula XI-A or XI-B in the reaction mixture in which they were formed to a temperature of from 0° to 40° C. Therefore, in accordance with this invention, there is no need to isolate the compounds of formula XI-A and XI-B from their reaction mixture. The reaction mixture containing the compounds of formula XI-A and XI-B can be warmed to a temperature of from 0° to 40° C. to form the compound of formula V. On the other hand, the compound of formula XI-A and XI-B can be isolated from the reaction mixture before warming has commenced.

Where it is desired to produce the compound of formula V where $R_6$ is
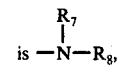

the compounds of formula IX-A and IX-B are converted to the compound of formula XI-A and XI-B where $R_5$ is

by conventional Claisen reaction utilizing conditions conventional in Claisen reactions with amides of either formulas XV-C or XV-D or mixtures thereof. In this reaction, the compounds of formula XI-B and XI-A where $R_5$ is

form as intermediates. This reaction is instantaneously converted under the conditions of the reaction to the compound of formula V. This reaction is carried out by reacting compounds of formula IX-A and IX-B with a compound of the formula XV-C or XV-D or mixtures thereof. This reaction is carried out at temperatures of from 120° C. to 250° C. in an inert organic solvent. Any conventional inert organic solvent can be utilized to carry out this reaction with high boiling solvents, i.e., solvents being above 120° C. being preferably utilized. Among the conventional inert organic solvents are included xylene and diglyme.

Where $R_6$ in the compound of formula V is other than hydrogen, the compound of formula V can be converted to the compound of the formula

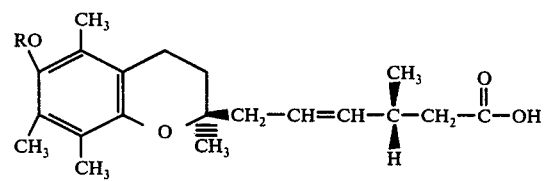

wherein R is as above
by hydrolysis by hydrolyzing the ester or amide group. Any conventional method of ester or amide hydrolysis can be utilized to affect this conversion. The silyl esters are also hydrolyzed to the compound of formula VI by conventional means. On the other hand, where $R_6$ in the compound of formula V is hydrogen, the aldehyde can be converted to the compound of the formula VI by oxidizing with a conventional oxidizing agent.

Any of the conventional oxidizing agents can be utilized. Among the preferred oxidizing agents are silver oxide and chromic oxide. Any of the conditions conventional in utilizing these oxidizing agents can be utilized to convert the aldehyde of formula V to the compound of formula VI.

In the next step of the process of this invention, the compound of formula VI is esterified with an esterification agent such as a reactive derivative of a lower alkanol to produce a compound of the formula

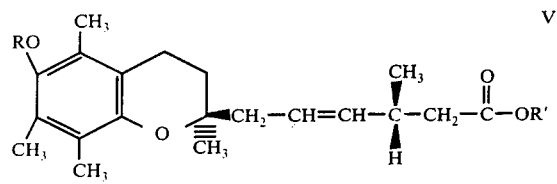

where R is as above and R' is lower alkyl.

The compound of formula V can be hydrogenated utilizing a metal hydrogenation catalyst to produce a compound of the formula

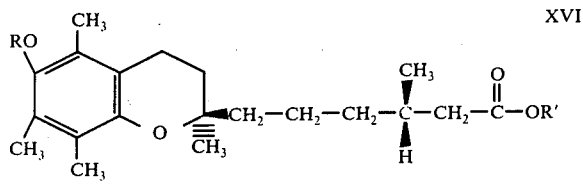

where R and R' are as above.

In this hydrogenation care should be utilized so that no more than one mole of hydrogen is utilized per mole of the compound XVI to prevent hydrogenation of the —OR group to —OH.

Any conventional hydrogenation procedure and metal hydrogenation catalyst can be utilized to carry out this procedure. Among the conventional metal hydrogenation catalysts are included palladium and platinum and Raney nickel.

The compound of formula XVI is next converted to a compound of the formula

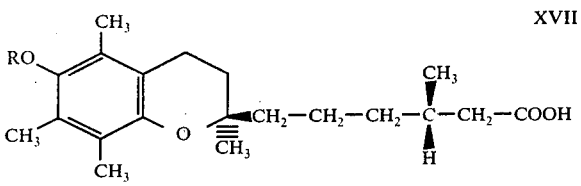

where R is as above
by alkaline or acid hydrolysis. Any conventional method of hydrolyzing an ester group by acid or alkaline hydrolysis can be utilized to carry out this procedure.

The compound of formula XVII is converted to the compound of formula

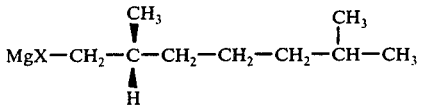

where R is as above
by reduction.

The compound of formula XVII can be converted into the compound of formula XVIII by first reducing the compound of formula XVII to the alcohol of formula XVIII. This reduction can be carried out by utilizing an aluminum hydride reducing agent. In utilizing an aluminum hydride reducing agent, any conventional aluminum hydride reducing agent can be utilized. Among the aluminum hydride reducing agents which can be utilized are included lithium aluminum hydride, sodium aluminum hydride, diisobutyl aluminum hydride, diisopropyl aluminum hydride, and sodium bis[2-methoxyethoxy]-aluminum hydride. This reduction is carried out in an inert organic solvent medium. Any conventional inert organic solvent can be utilized in carrying out this reaction. Among the preferred inert organic solvents are included tetrahydrofuran, dioxane, diethyl ether, hexane, toluene, benzene or xylene. This reaction can be carried out at room temperature, i.e., 25° C., and atmospheric pressure. On the other hand, reduced or elevated temperatures can be utilized, i.e., from −30° C. to about 140° C., with temperatures of from 25° C. to 60° C. being preferred.

The compound of formula XVIII is next converted to the compound of the formula

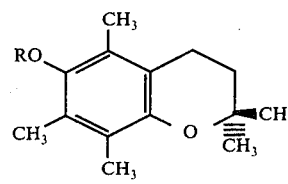

wherein R is as above and $OR_{12}$ is a leaving group.

The compound of formula XIX is reacted with a compound of the formula $$MgX-CH_2-\underset{H}{\overset{CH_3}{C}}-CH_2-CH_2-CH_2-\overset{CH_3}{CH}-CH_3 \qquad XX$$

wherein X is halogen
to form a compound of the formula

XXI

[structure: RO-aryl-O-CH₂-CH₂-CH₂-C(CH₃)(H)-CH₂-CH₂-CH₂-C(CH₃)(H)-CH₂-CH₂-CH₂-CH(CH₃)-CH₃]

wherein R is as above.

The compound of formula XIX can be prepared from the compound of formula XVIII by converting the free hydroxy group in the compound of formula XVIII to a leaving group. Any conventional method of converting a hydroxy group to a leaving group can be utilized. Among the preferred methods is to react the compound of formula XVIII with an aryl sulfonyl halide such as naphthylsulfonyl halide, p-toluene sulfonyl halide, etc. or a lower alkyl sulfonyl halide such as methylsulfonyl halide in the presence of an organic amine base such as pyridine, triethyl amine, etc.

In the compound of formula XIX, $OR_{12}$ can be any conventional leaving group. Among the preferred leaving groups formed by $—OR_{12}$ are alkyl sulfonyloxy such as methylsulfonyloxy, arylsulfonyloxy, such as p-toluenesulfonyloxy, naphthylsulfonyloxy, etc.

The compounds of formulas XIX and XX are reacted to form the compound of formula XXI in the presence of a di(alkali metal)tetrahalocuprate utilizing the procedure disclosed by Fouquet and Schlosser on pages 82 and 83 of *Angew. Chem. Internat. Edit.,* Volume 13 (1974). In the procedure disclosed by Fouquet and Schlosser, carbon to carbon linkage of hydrocarbons is carried out through the reaction of a magnesium halide with a sulfonyl ester. In this reaction, any conventional di(alkali metal)tetrahalocuprate can be utilized with dilithium tetachlorocuprate being preferred. Generally, this reaction is carried out in the presence of an ether solvent. Any conventional inert organic ether solvent can be utilized. Among the preferred solvents are included tetrahydrofuran, dioxane, diethyl ether, dimethoxyethane, diglyme, etc.

The compound of formula XXI can be converted to the compound of formula I by hydrogenation in the presence of a hydrogenation catalyst such as palladium, platinum, Raney nickel, etc. Any conventional method of hydrogenation can be utilized to make this conversion.

The compound of formula XX and its method of preparation is disclosed in Ser. No. 544,163 filed Jan. 27, 1973, Cohen and Saucy. Note the compound of formula IX in Ser. No. 544,163 where n is 0, $R_5$ is $—CH_2MgX$ and A and B are hydrogen. Also note Examples 10 and 12 of Ser. No. 544,163. The disclosure of this application, Ser. No. 544,163, filed Jan. 27, 1973, is incorporated by reference.

As used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aroic acid" comprehends acids wherein the aryl group is defined as above. The preferred aroic acid is benzoic acid. The term "ether protecting group removable by hydrogenolysis" designates any ether which, upon hydrogenolysis yields the hydroxy group. A suitable ether protecting group is arylmethyl ethers such as benzyl, benzhydryl or trityl ethers.

The preferred ethers which are removable by hydrogenolysis are the aryl methyl ethers such as benzyl or substituted benzyl ethers. The hydrogenolysis can be carried out by hydrogenation in the presence of a suitable hydrogenation catalyst. Any conventional method of hydrogenation can be utilized in carrying out this procedure. Any conventional hydrogenation catalyst such a palladium or platinum can be utilized.

The following examples are illustrative but not limitative of the invention. All temperatures are in degrees Centigrade and the ether is diethyl ether. the term "5% Pd-C" designates a carbon catalyst containing 5% by weight palladium and 95% by weight carbon. The term "THF" designates tetrahydrofuran and the term "HMDA" describes hexamethylenephosphoramide. The term "concentrated aqueous hydrochloric acid" designates 10N hydrochloric acid. The term "Kugelrohr" designates evaporation distillation. The term "Lindlar catalyst" designates a catalyst prepared from palladium, calcium carbonate and lead acetate as described in Organic Synthesis Collective, Volume 5, pages 880–883 (1973).

EXAMPLE 1

Preparation of
2(S)-[2(R)-hydroxy-3-pentynyl]-2,5,7,8-tetramethyl-6-benzyloxychroman and
2(S)-[2(S)-hydroxy-3-pentynyl]-2,5,7,8-tetramethyl-6-benzyloxychroman To an excess of propynyl magnesium bromide (approximatey 2.5 equivalents) in 1.0 liter of dry ether was added 64 g. (0.189 mol) of (S)-6-benzyloxy-2,5,7,8-tetramethylchrom-2-acetaldehyde in 1.0 liter of dry ether, at 0°–4° C. with mechanical stirring. When addition was complete, the reaction mixture was further stirred at 0° C for ½ hour and then 25° C. for ½ hour. The reaction mixture was poured in small portions into 500 ml. of saturated aqueous $NH_4Cl$ solution. It was extracted with diethyl ether (4 × 250 ml.). The combined ether extract was washed with water (3 × 200 ml.), dried over $MgSO_4$ and concentrated at reduced pressure. Crystallization of the crude product from diethyl ether-petroleum ether (30°–60° C.) yielded 27.5 g. of 2(S)-[2(R)-hydroxy-3-pentynyl]2,5,7,8-tetramethyl-6-benzyloxychroman, m.p. 89°–91° C.

The mother liquor from the above was concentrated to dryness and crystallized from ether-hexane to give 5.01 g. of 2(S)-[2(S)-hydroxy-3-pentynyl]-2,5,7,8-tetramethyl-6-benzyloxychroman as white crystals, m.p. 74°–76° C. $[\alpha]_D^{25}$ −42.01°.

EXAMPLE 2

Preparation of
2(S)-[2(R)-hydroxy-3(E)-pentenyl]-2,5,7,8-tetramethyl-6-benzyloxychroman To a solution of 5.0 g. (13.32 mmol) of 2(S)-[2(R)-hydroxy-3-pentynyl]-2,5,7,8-tetramethyl-6-benzyloxychroman in 50 ml. of dry ether was carefully added 4.06 ml. of sodium bis (2-methoxyethoxy)-aluminum hydride (29 mg.-atm. of hydrogen) in 10 ml. of dry ether. The resulting solution was refluxed under argon for 17 hours. The solution was cooled in an ice bath and 10% by volumn aqueous $H_2SO_4$ solution (100 ml.) was carefully added. It was filtered, washed with ether and water. The aqueous phase was again extracted with ether (3 × 100 ml.). The combined ether phase was washed with saturated aqueous $NaHCO_3$ solution (3 × 50 ml.) and water (3 × 50 ml.) and dried over $MgSO_4$. Evaporation of ether to dryness at reduced pressure yielded 5.206 g. of crude product which was crystallized from petroleum ether (b.p. 30°–60° C.) to give 4.23 g. of 2(S)-[2(R)-hydroxy-3(E)-pentenyl]-2,5,7,8-tetramethyl-6-benzyloxychroman as white needles, m.p. 68°–70° C. $[\alpha]_D^{25} -24.02°$ (CHCl$_3$).

EXAMPLE 3

Preparation of 2(S)-[2(S)-hydroxy-3(Z)-pentenyl]-2,5,7,8-tetramethyl-6-benzyloxychroman 2.5 g. of 2(S)-[2(S)-hydroxy-3-pentynyl]-2,5,7,8-tetramethyl-6-benzyloxychroman and 0.25 g. of Lindlar catalyst in 15 ml. of ethyl acetate-hexane (2 = 1 parts by volume) containing 0.1 ml. of quinoline was hydrogenated at 25° C. and atmospheric pressure. The catalyst was filtered off and washed with ethyl acetate. The ethyl acetate solution was washed with 1.0 N aqueous HCl (3 × 50 ml.), water (3 × 50 ml.) and dried over MgSO$_4$ and concentrated in vacuo to give 2.508 g. of crude product. Crystallization of this material from pentane yielded 2.053 g. of 2(S)-[2(S)-hydroxy-3(Z)-pentenyl]-2,5,7,8-tetramethyl-6-benzyloxychroman as white crystals, m.p. 84°–86° C. $[\alpha]_D^{25} -30.57°$ (CHCl$_3$).

EXAMPLE 4

Preparation of 6-[2(S)-6-benzyloxy-2,5,7,8-tetramethyl-2-chromanyl]-3(R)-methyl-4(E)-hexenoic acid, ethyl ester To 4.42 g. (1.16 mmol) of 2(S)-[2(R)-hydroxy-3(E)-pentenyl]-2,5,7,8-tetramethyl-6-benzyloxychroman was added 13.10 g. (8.12 mmol) of triethylortho acetate and 85.5 mg. (0.116 mmol) of propionic acid. The solution was degassed with argon and refluxed for 4.0 hours while the ethanol formed was distilled off. The excess of reagent was removed in vacuo and the oily crude product was passed over 125 g. of silica gel. Elution with 1:4 parts by volume diethyl ether-petroleum ether (30°–60°) afforded 4.86 g. (92% yield) of 6-[2(S)-6-benzyloxy-2,5,7,8-tetramethyl-2-chromanyl]-3(R)-methyl-4(E)-hexenoic acid, ethyl ester as colorless oil, $[\alpha]_D^{25} +0.91°$ (c 5.0475, CHCl$_3$).

EXAMPLE 5

By the procedure of Example 4, 105 g. of 6-[2(S)-6-benzyloxy-2,5,7,8-tetramethyl-2-chromanyl]-3(R)-methyl-4(E)-hexenoic acid, ethyl ester was prepared from 1.0 g. of 2(S)-[2(S)-hydroxy-3(Z))-pentenyl]-2,5,7,8-tetramethyl-6-benzyloxychroman, 3.0 g. of triethylortho acetate and 19.5 mg. of propionic acid.

EXAMPLE 6

Preparation of 6-[2(S)-6-benzyloxy-2,5,7,8-tetramethyl-2-chromanyl]-3(R)-methyl-4(E)-hexenoic acid A solution of 2.0 g. (0.44 mmol) of 6-[2(S)-6-benzyloxy-2,5,7,8-tetramethyl-2-chromanyl]-3(R)-methyl-4(E)-hexenoic acid, ethyl ester in 7 ml. of methanol and 2 ml. of 6.0 N NaOH was refluxed for 2.0 hours. The solution was diluted with water (ca. 150 ml.) and extracted with ether (2 × 30 ml.). The aqueous alkaline phase was cooled in an ice bath and then acidified with concentrated hydrochloric acid. It was extracted with ether (5 × 50 ml.). The combined ether extract was washed twice with saturated aqueous NH$_4$Cl and dried over MgSO$_4$. Evaporation of ether to dryness in vacuo yielded 1.57 g. of 6-[2(S)-6-benzyloxy-2,5,7,8-tetramethyl-2-chromanyl]-3(R)-methyl-4(E)-hexenoic acid, as colorless oil (84% yield), $[\alpha]_D^{25} -2.73°$.

EXAMPLE 7

Preparation of 6-[2(R)-6-benzyloxy-2,5,7,8-tetramethyl-2-chromanyl]-3(S)-methylhexanoic acid, ethyl ester 3.36 g. of 6-[2(S)-6-benzyloxy-2,5,7,8-tetramethyl-2-chromanyl]-3(R)-methyl-4(E)-hexenoic acid, ethyl ester and 350 mg. of 5% palladium on charcoal was hydrogenated in 20 ml. of ethyl acetate at 23° and one atmosphere until one equivalent of hydrogen was consumed. The catalyst was filtered off and was washed with ethyl acetate. Evaporation of solvent to dryness in vacuo gave 3.07 g. of 6-[2(R)-6-benzyloxy-2,5,7,8-tetramethyl-2-chromanyl]-3(S)-methylhexanoic acid, ethyl ester as colorless oil, $[\alpha]_D^{25} -0.22°$ (c 4.135, CHCl$_3$).

EXAMPLE 8

Preparation of 6-[2(R)-6-benzyloxy-2,5,7,8-tetramethyl-2-chromanyl]-3(S)-methylhexanoic acid, ethyl ester 6-[2(S)-6-benzyloxy-2,5,7,8-tetramethyl-2-chromanyl]-3(R)-methyl-4(E)-hexenoic acid, ethyl ester (1.0 g., 2.2 mmol) was hydrogenated over 200 mg. of Raney nickel in ethyl acetate (25 ml.) at 25° C., 30 p.s.i.g. for 4.0 hours. The Raney nickel was filtered off and washed well with ethyl acetate. Evaporation of ethyl acetate to dryness in vacuo gave 1.005 g. of colorless oil. This was dissolved in dimethylformamide (10 ml.) and treated with 532 mg. (3.8 mmol) of anhydrous potassium carbonate and 435 mg. (3.8 mmol) of benzyl chloride at 25° for 60 hours. The reaction mixture was diluted with water (150 ml.) and extracted with ether (3 × 70 ml.). The combined ether extract was washed with water (3 × 30 ml.), once with saturated brine (50 ml.) and dried over anhydrous MgSO$_4$. Evaporation of ether to dryness in vacuo yielded 930 mg. of crude product which was purified by column chromatography on 40 g. of silica gel. Elution with ether-petroleum ether (3:7) gave 650 mg. of pure 6-[2(R)-6-benzyloxy-2,5,7,8-tetramethyl-2-chromanyl]-3(S)-methylhexanoic acid, ethyl ester.

EXAMPLE 9

Preparation of 6-[2(R)-6-benzyloxy-2,5,7,8-tetramethyl-2-chromanyl]-3(S)-methylhexanoic acid 600 Mg. (1.33 mmol) of 6-[2(R)-6-benzyloxy-2,5,7,8-tetramethyl-2-chromanyl]-3(S)-methylhexanoic acid, ethyl ester was refluxed for 2.0 hours in 10 ml. of methanol and 2 ml. of 6N NaOH. The reaction mixture was cooled to room temperature and diluted with water and washed with ether. The alkaline aqueous phase was cooled in an ice bath and acidified with concentrated hydrochloric acid. It was then extracted with ether. The ether extracts were combined, washed with three portions of saturated NH$_4$Cl solution and dried over anhydrous MgSO$_4$. Evaporation of the ether to dryness in vacuo gave the oily crude acid, which was quickly filtered through a column of silica gel (10 g.) and elution with CHCl$_3$ yielded 510 mg. (90% yield) of 6-[2(R)-6-benzyloxy-2,5,7,8-tetramethyl-2-chromanyl]-3(S)-methylhexanoic acid as colorless oil, $[\alpha]_D^{25} -1.66°$ (c 1.9288, CHCl$_3$).

EXAMPLE 10

Preparation of 6-[2(R)-6-benzyloxy-2,5,7,8-tetramethyl-2-chromanyl]-3(S)-methylhexanol To a solution of 2.20 g. (4.85 mmol) of 6-[2(R)-6-benzyloxy-2,5,7,8-tetramethyl-2-chromanyl]-3(S)-methylhexanoic acid, ethyl ester in 20 ml. of dry ether was slowly added 0.81 ml. (5.82 mmol) of sodium bis-(2-methoxyethoxy)aluminum hydride (70% in benzene) in 2 ml. of dry ether. The solution was refluxed for 1.0 hour. An additional 1 ml. of sodium bis-(2-methoxyethoxy) aluminum hydride was added again and it was refluxed for 2.0 hours more. The reaction mixture was cooled to 0° C. and excess of hydride ws destroyed by carefully adding 10 ml. of 1.0 N $H_2SO_4$ followed by 100 ml. of water. The precipitate was filtered off and washed well with ether. The aqueous phase was separated and extracted with ether (3 × 60 ml.). The combined ether extract was washed with water (2 × 30 ml.), saturated brine (30 ml.) and dried over anhydrous $MgSO_4$. Evaporation of ether to dryness in vacuo gave 2.175 g. of crude product which was chromatographed on 100 g. of silica gel. Elution with 3-7 parts by volume ether-petroleum ether afforded 1.55 g. (78% yield) of 6-[2(R)-6-benzyloxy-2,5,7,8-tetramethyl-2-chromanyl]-3(S)-methylhexanol as a colorless oil, $[\alpha]_D^{25} -0.59°$ (c 1.010, $CHCl_3$).

EXAMPLE 11

Preparation of 6-[2(R)-6-benzyloxy-2,5,7,8-tetramethyl-2-chromanyl]-3(S)-methylhexanol p-toluenesulfonate To 1.226 g. (2.98 mmol) of 6-[2(R)-6-benzyloxy-2,5,7,8-tetramethyl-2-chromanyl]-3(S)-methylhexanol in 4 ml. of dry pyridine (dried and distilled over barium oxide) was added in portions 1.14 g. (5.96 mmol) of p-toluene-sulfonyl chloride at 0° C. The resulting solution was stirred at 0° C. for 3.0 hours and then kept in the refrigerator for 16 hours. The mixture was poured into 100 ml. of ice water and acidified with 3N HCl (about 50 ml.). It was extracted with ether (3 × 70 ml.). The combined ether extract was washed with water (3 × 30 ml.) and dried over anhydrous potassium carbonate-sodium sulfate (ca. 1 = 1). Evaporation of ether to dryness in vacuo yielded 1.804 g. of 6-[2(R)-6-benzyloxy-2,5,7,8-tetramethyl-2-chromanyl]-3(S)-methylhexanol p-toluenesulfonate as yellow oil, ms = m/e 564 ($M^+$).

EXAMPLE 12

Preparation of (2R, 4'R, 8'R)-α-tocopherol benzyl ether

To 195 mg. (8.0 mmol) of powdered magnesium in 3 ml. of dry THF was added dropwise 1.24 g. (6.00 mmol) of 2(R)-6-dimethylheptyl-1-magnesium bromide (prepared from (R)-1-bromo-2,6-dimethylheptane) in 3 ml. of dry THF. The reaction mixture was stirred and refluxed under argon for 3.0 hours and then at 25° for 1.0 hour. It was then cooled to −78° C. in a dry ice-acetone bath and to this solution was added 0.1 ml. of $LiCuCl_4$, followed by 0.64 g. (1.14 mmol) of 6-[2(R)-6-benzyloxy-2,5,7,8-tetramethyl-2-chromanyl]-3(S)-methylhexanol p-toluenesulfonate in 10 ml. of THF. It was stirred at −78° for 10 minutes and then allowed to warm to 25° and stirred for 17 hours under argon. The mixture was treated with 5 ml. of 1N aqueous $H_2SO_4$ and was worked up by ether extraction giving 1.026 g. of crude product. This material was purified by thick layer chromatography on silica gel and elution with ethyl ether-hexane (5 = 95) afforded 406 mg. of (2R, 4'R, 8'R)-α-tocopherol benzyl ether (69% yield).

EXAMPLE 13

Preparation of (2R, 4'R, 8'R)-α-tocopheryl acetate (2R, 4'R, 8'R)-α-Tocopherol benzyl ether (326 mg., 0.626 mmol) and 60 mg. of 5% palladium on carbon was hydrogenated in 5 ml. of THF containing two drops of concentrated hydrochloric acid at 25° C. and atmospheric pressure for 1-½ hour. The catalyst was filtered off and washed well with ethyl acetate. Evaporation of ethyl acetate to dryness at reduced pressure gave 239 mg. of (2R, 4'R, 8'R)-α-tocopherol as a light yellow oil. This material was treated with 2 ml. of dry pyridine and 2 ml. of acetic anhydride at 25° for 16 hours. The mixture was poured into ice water (25 ml.) and extracted with chloroform (3 × 50 ml.). The combined chloroform extract was successively washed with 1.0 N aqueous HCl (3 × 20 ml.), saturated aqueous $NaHCO_3$ solution (3 × 20 ml.), water (3 × 20 ml.) and dried over anhydrous $MgSO_4$. Evaporation of solvent to dryness in vacuo gave 250 mg. of crude product. This material was purified by thick layer chromatography on silica gel and elution with ether-petroleum ether (1:4) afforded 188 mg. (63.7% from benzyl ether) of pure (2R, 4'R, 8'R)-α-tocopheryl acetate as a slightly yellow oil, $[\alpha]_D^{25} +2.59°$.

We claim:

1. A compound of the formula:

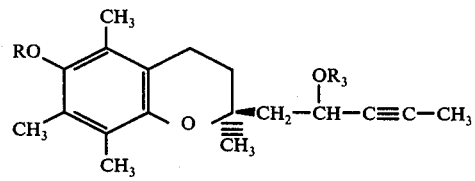

wherein R is benzyl, benzhydryl or trityl; and $R_3$ is 3,5-dinitrobenzoyl, p-nitrobenzoyl or benzoyl.

* * * * *